United States Patent
Busch

Patent Number: 5,813,407
Date of Patent: Sep. 29, 1998

[54] BLANKET WITH PERMEABLE WINDOW

[76] Inventor: Michael C. Busch, 124 Seaside Cir., Ponte Vedra Beach, Fla. 32082

[21] Appl. No.: 863,346

[22] Filed: May 27, 1997

[51] Int. Cl.⁶ .................................................... A61B 19/00
[52] U.S. Cl. ............................................ 128/849; 128/853
[58] Field of Search ...................... 128/849–856; 5/421, 423, 482; 607/104

[56] References Cited

U.S. PATENT DOCUMENTS

| | | | |
|---|---|---|---|
| 4,367,728 | 1/1983 | Mutke | 128/853 |
| 4,384,573 | 5/1983 | Elliott | 128/853 |
| 4,745,915 | 5/1988 | Enright | 128/853 |
| 5,184,612 | 2/1993 | Augustine | 128/400 |
| 5,300,102 | 4/1994 | Augustine et al. | 607/107 |
| 5,324,320 | 6/1994 | Augustine et al. | 607/107 |
| 5,336,250 | 8/1994 | Augustine et al. | 607/107 |
| 5,343,579 | 9/1994 | Dickerhoff et al. | 5/421 |
| 5,360,439 | 11/1994 | Dickerhoff | 607/104 |
| 5,384,924 | 1/1995 | Dickerhoff | 5/421 |
| 5,392,847 | 2/1995 | Stephenson | 165/46 |
| 5,405,371 | 4/1995 | Augustine et al. | 607/107 |
| 5,443,488 | 8/1995 | Namenye et al. | 607/104 |
| 5,490,524 | 2/1996 | Williams | 128/853 |
| 5,514,169 | 5/1996 | Dickerhoff | 607/107 |

*Primary Examiner*—Michael A. Brown

[57] ABSTRACT

A blanket with permeable window (10) has a blanket (12). The blanket with permeable window (10) further has at least one permeable transparent window (14) positioned within the blanket (12). A periphery of the at least one permeable transparent window (14) is securely attached to the blanket (12) by at least one fastener (20). The at least one permeable transparent window (14) functions to allow viewing of an intravenous tube (18A) and intravenous needle (18B) of an intravenous (18) which is positioned within a patient appendage vein (16AA) of a patient appendage (16A) of a patient (16).

4 Claims, 4 Drawing Sheets

BLANKET WITH PERMEABLE WINDOW

BACKGROUND OF THE INVENTION

1. Field of the Invention

The present invention relates to blankets with windows. More particularly, the present invention relates to blankets with at least one window screen which functions to allow viewing of an intravenous needle of an intravenous tube inserted in a patient appendage vein.

2. Description of the Prior Art

History shows that patients on hemodialysis get cold while sitting in chairs for hours and receiving their treatments. A problem then is they cover themselves with a blanket, including their access site. The access site is typically in their arms; sometimes in their legs or upper thigh.

The patient's limbs get cold from air conditioning and drafts. The patients then cover their site with a blanket. An observer cannot see where the needles enter the site or the blood tubing connections are to the needles. Typical blood flow is 400 cc per minute, and a dislodged needle can cost a patient their life. There have been reports of patients bleeding to death, others requiring hospitalization, transfusions, etc. All because the clinician could not view the event in a proper response time.

Numerous innovations for blankets with windows have been provided in the prior art that are described as follows. Even though these innovations may be suitable for the specific individual purposes to which they address, they differ from the present invention as hereinafter contrasted.

In U.S. Pat. No. 5,343,579, titled Warming Blanket having Multiple Inlets, invented by Scott D. Dickerhoff, Thomas F. Kappel and Robert A. Virag, the present invention relates to a blanket for use with forced air convection systems, wherein the blanket includes multiple inlet ports. By providing a blanket with multiple inlets, the user has the choice of positioning the air supply or blower unit and the supply hose on either side of the patient. In addition, in a preferred embodiment, the inlet ports are resealable, thus allowing the user to switch inlets during use.

The patented invention differs from the present invention because the patented invention is a blanket for use with forced air convection systems. Heated air is forced through multiple opening in a blanket structure. The blanket is heated and heated air exhausts through openings in the surface of the blanket. The present invention comprises a insulating material with a mesh screen window located proximal to a access area. The present invention lacks the forced air feature of the patented invention.

In U.S. Pat. No. 5,443,488, titled Thermal Blanket with Surgical Access, invented by Joseph A. Namenye, James G. Stephenson and Corrie T. M. Anderson, a disposable pneumatic thermal blanket for controlling a patient's body temperature wherein the blanket includes structure for providing access through the blanket for surgical purposes. The inflatable blanket consists of upper and lower thermoplastic sheets heat sealed at the periphery and specified locations and sealed slits within the blanket central region permit access to a patient without loss of temperature controlled air. The blanket includes strategically placed adhesive strips or patches to aid the positioning of folded blanket access portions, or positioning of the blanket on the patient, and the location and relationship of the slits permit a variety of shapes and sizes of access openings to be selectively formed.

The patented invention differs from the present invention because the patented invention is a blanket for use with forced air convection systems. Heated air is forced through multiple opening in a blanket structure. The patented invention has portions which permits access to various sites for surgery. The present invention comprises a insulating material with a mesh screen window located proximal to a access area. The present invention lacks the forced air feature of the patented invention.

In U.S. Pat. No. 5,324,320, titled Thermal Blanket, invented by Scott D. Augustine and Douglas J. Augustine, a thermal blanket includes an inflatable covering with a head end, a foot end, two edges and an undersurface. The covering includes a plurality of inflatable chambers that are inflated when a thermally-controlled inflating medium is introduced into the thermal blanket through an inlet at the foot end. When inflated, the thermal blanket self-erects into a structure and provides a bath of thermally-controlled inflating medium to the interior of the erected structure through an aperture array on the undersurface of the inflatable covering. The thermal blanket includes a first aspect in which the inflatable chambers in the covering are oriented for substantially longitudinal disposition over a portion of a patient's body extending from the pelvic area to the feet of the patient's body. This aspect may include a provision for securing the inflatable covering to the patient's body at the head end and an non-inflatable foot drape at the foot end. In another aspect of the thermal blanket, the inflatable chambers are oriented for substantially transverse disposition over a portion of the patient's body extending across the arms and chest of the patient's body. This aspect may include an non-inflatable portion at the foot end of the thermal blanket with provision for attaching to a patient's body and a head drape at the head end to drape over the patient's head.

The patented invention differs from the present invention because the patented invention is a thermal blanket includes an inflatable covering. Heated air function to heat the blanket. The patented invention lacks the access feature of the present invention.

In U.S. Pat. No. 5,392,847, titled Thermal Medical Blanket using Internal Subtube, invented by James G. Stephenson, a pneumatic, disposable, temperature control blanket pressurized with a heated or cooled air comprises an inflated envelope having a lower sheet having openings formed therein for impinging the air upon a patient. Air is introduced into the blanket envelope at a single inlet port, and an interior flexible conduit or subtube located within the envelope communicates with the inlet for distributing freshly introduced air throughout the blanket length with little temperature loss.

The patented invention differs from the present invention because the patented invention is a blanket for use with forced air convection systems. Heated air is forced through multiple opening in a blanket structure. The present invention comprises a insulating material with a mesh screen window located proximal to a access area. The present invention lacks the forced air feature of the patented invention.

In U.S. Pat. No. 5,384,924, titled Warming Blanket having Multiple Inlets, invented by Scott D. Dickerhoff Thomas F. Kappel and Robert A. Virag, the present invention relates to a blanket for use with forced air convection systems, wherein the blanket includes multiple inlet ports. By providing a blanket with multiple inlets, the user has the choice of positioning the air supply or blower unit and the supply hose on either side of the patient. In addition, in a preferred embodiment, the inlet ports are resealable, thus allowing the user to switch inlets during use.

The patented invention differs from the present invention because the patented invention is a blanket for use with forced air convection systems, wherein the blanket includes multiple inlet ports. The present invention is a blanket having insulation properties. The blanket includes at least one mesh screen located such that it is proximal to an access site. The access site preferably is one for a intravenous connection. The blanket and mesh screen are washable and sterilizable. The significant advantage is that the access area can be observed with out removing the blanket or disturbing the patient.

In U.S. Pat. No. 5,360,439, titled Warming Blanket Method Utilizing a Warming Blanket having Multiple Inlets, invented by Scott D. Dickerhoff, Thomas F. Kappel and Robert A. Virag, the present invention relates to a method for warming a patient with a blanket used with forced air convection systems, wherein the blanket includes multiple inlet ports. By providing a blanket with multiple inlets, the user has the choice of positioning the air supply or blower unit and the supply hose on either side of the patient. In addition, in a preferred embodiment, the inlet ports are resealable, thus allowing the user to switch inlets during use.

The patented invention differs from the present invention because the patented invention is a blanket for use with forced air convection systems. Heated air is forced through multiple opening in a blanket structure. The blanket is heated and heated air exhausts through openings in the surface of the blanket. The present invention comprises a insulating material with a mesh screen window located proximal to a access area. The present invention lacks the forced air feature of the patented invention.

In U.S. Pat. No. 5,514,169, titled Warming Blanket having Multiple Inlets, invented by Scott D. Dickerhoff, Thomas F. Kappel and Robert A. Virga, the present invention relates to a blanket for use with forced air convection systems, wherein the blanket includes multiple inlet ports. By providing a blanket with multiple inlets, the user has the choice of positioning the air supply or blower unit and the supply hose on either side of the patient. In addition, in a preferred embodiment, the inlet ports are resealable, thus allowing the user to switch inlets during use.

The patented invention differs from the present invention because the patented invention is a blanket for use with forced air convection systems. Heated air is forced through multiple opening in a blanket structure. The blanket is heated and heated air exhausts through openings in the surface of the blanket. The present invention comprises a insulating material with a mesh screen window located proximal to a access area. The present invention lacks the forced air feature of the patented invention.

In U.S. Pat. No. 5,184,612, titled Thermal Blanket with Transparent Upper Body Drape, invented by Scott D. Augustine, a thermal blanket of the Augustine type includes an inflatable covering with a head end, a foot end, two edges and an undersurface. The covering is inflated through an inlet by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover toward the periphery of the thermal blanket. A pair of non-inflatable drape sections are provided at the head end for covering the chest area and enabling viewing thereof When inflated, the thermal blanket self-erects and provides a bath of thermally-controlled inflating medium to the interior of the erected structure. When the structure covers a patient, the non-inflatable transparent section at the head end provides a relatively unobstructed view of the sides of the patient's chest and upper torso.

The patented invention differs from the present invention because the patented invention is a thermal blanket includes an inflatable covering. Heated air function to heat the blanket. The patented invention lacks the access feature of the present invention. In U.S. Pat. No. 5,405,371, invented by Scott D. Augustine and Randall C. Arnold, a thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally-controlled inflating medium from the covering. Exhaust port openings are provided at the edges of the covering to vent the inflating medium, which enhances circulation of the thermally-controlled medium through the cover. An non-inflatable section is provided at the head end, together with an absorbent bib attached to the covering, adjacent the non-inflatable section. When inflated, the thermal blanket self-erects and provides a bath of thermally-controlled inflating medium to the interior of the erected structure. The enhanced circulation of the medium through the covers maintains a relatively high average temperature under the blanket and a relatively uniform distribution of temperature in the inflating medium which is exhausted through the apertures into the structure's interior. When the structure covers a patient, the non-inflatable section provides a relatively unobstructed view of the patient's face, while the absorbent bib maintains a relatively sanitary environment in the area beneath the patient's head.

The patented invention differs from the present invention because the patented invention is a thermal blanket includes an inflatable covering. Heated air function to heat the blanket. The patented invention lacks the access feature of the present invention.

In U.S. Pat. No. 5,300,102, titled Thermal Blanket invented by Scott D. Augustine and Randall C. Arnold A thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover. An non-inflatable section is provided at the head end, together with an absorbent bib attached to the covering, adjacent the non-inflatable section. An non-inflatable section may also be provided at the foot end having a pair of seams to form an erectable drape section. The enhanced circulation of the medium through the covers maintains a relatively high average temperature under the blanket and a relatively uniform distribution of temperature in the inflating medium which is exhausted through the apertures into the structure's interior. When the structure covers a patient, the non-inflatable section at the head end provides a relatively unobstructed view of the patient's face, while the absorbent bib maintains a relatively sanitary environment in the area beneath the patient's head. The non-inflatable section at the foot end retains heat from the inflating medium to warm the patient's feet and insulate the bare skin of the feet from excessive conductive heat from the hose connected to the inflation inlet.

The patented invention differs from the present invention because the patented invention is a thermal blanket includes an inflatable covering. Heated air function to heat the blanket. The patented invention lacks the access feature of the present invention.

In U.S. Pat. No. 5,336,250, titled Thermal Blanket with Transparent Upper Body Drape, invented by Scott D. Augustine, a thermal blanket of the Augustine type includes an inflatable covering with a head end, a foot end, two edges and an undersurface. The covering is inflated through an inlet by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover toward the periphery of the thermal blanket. A pair of non-inflatable drape sections are provided at the head end for covering the chest area and enabling viewing thereof. When inflated, the thermal blanket self-erects and provides a bath of thermally-controlled inflating medium to the interior of the erected structure. When the structure covers a patient, the non-inflatable transparent section at the head end provides a relatively unobstructed view of the sides of the patient's chest and upper torso.

The patented invention differs from the present invention because the patented invention is a thermal blanket includes an inflatable covering. Heated air function to heat the blanket. The patented invention lacks the access feature of the present invention.

Numerous innovations for blankets with windows have been provided in the prior art that are adapted to be used. Even though these innovations may be suitable for the specific individual purposes to which they address, they would not be suitable for the purposes of the present invention as heretofore described.

SUMMARY OF THE INVENTION

The present invention allows the operator to view the access site through a white 300 mesh screen. With the limb resting on a white cloth or sheet, the contrast is excellent; should there be blood escaping, it can be seen easily. The patient complains when their covers are removed to view their site, often because they are sleeping at the time, not to mention the cold. The present invention, allows an observer to view the access site without disturbing the patient and keeps them warm as well.

The blanket is machine washable, one size for hemodialysis patients, reversible for left or right access, and invertible for arm to leg accesses. The screen reduced heat loss and reduces drafts up to 90%. 48 inch by 72 inch for Hemodialysis with a 12 inch by 24 inch screen.

The present invention is not solely used for Hemodialysis. In hospital settings, they can be made to any size. The screen can be placed anywhere needed to view the dressing, IV, chest tubes, drainage tubes, etc., smaller sizes for pediatrics.

Prototypes have been used by patients and they love it! The Observation Staff loved it too. They felt much more comfortable being able to glance at the access sites at a moment's notice, without disturbing the patient.

The present invention allows a caretaker to visually inspect a person's access site (i.e., IV, catheter, etc., or wound covering, i.e., dressing from abdominal surgery) without removing the cover or blanket and/or disturbing the person (patient). The purpose of the screen is to see the "site" without removing the cover. Thus, providing more comfort for the patient and safely allowing the coverage of the site, during convalescence or therapeutical treatment. The screen also allows air circulation, yet inhibits drafts and cold. Completely washable and dryable, as well as sterilizable. Commercial laundry and/or ETO. Residential use and laundry is also tolerable.

The types of problems encountered in the prior art are blankets do not allow viewing.

In the prior art, unsuccessful attempts to solve this problem were attempted namely: plastic transparent non-permeable windows. However, the problem was solved by the present invention because the window is transparent and permeable.

Innovations within the prior art are rapidly being exploited in the field of patient care.

The present invention went contrary to the teaching of the art which describes and claims non-permeable windowed blankets.

The present invention solved a long felt need for a permeable window blanket.

The present invention produced unexpected results namely: allowing perspiration to escape which minimizes infection at the point of entry.

A synergistic effect was produced utilizing the present invention due to the following facts and results from experimentation: reducing infection improved the overall health of the patient and minimized hospital care.

Accordingly, it is an object of the present invention to provide a blanket with permeable window having a blanket and a permeable transparent window.

More particularly, it is an object of the present invention to provide the blanket having a blanket top and a blanket bottom with blanket fill therebetween.

In keeping with these objects, and with others which will become apparent hereinafter, one feature of the present invention resides, briefly stated, in the permeable transparent window allowing patient perspiration to escape.

When the blanket with permeable window is designed in accordance with the present invention, the blanket with permeable window machine is washable and dry cleanable.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

LIST OF REFERENCE NUMERALS UTILIZED IN THE DRAWINGS

10 - blanket with permeable window (10)
12 - blanket (12)
12T - blanket top (12T)
12B - blanket bottom (12B)
12C - blanket till (12C)
14 - permeable transparent window (14)
16 - patient (16)
16A - patient arm (16A)
16AA - patient arm vein (16AA)
18 - intravenous (18)
18A - intravenous tube (18A)
18B - intravenous needle (18B)
20 - fastener (20)

DESCRIPTION OF THE PREFERRED EMBODIMENT

Figure 1:
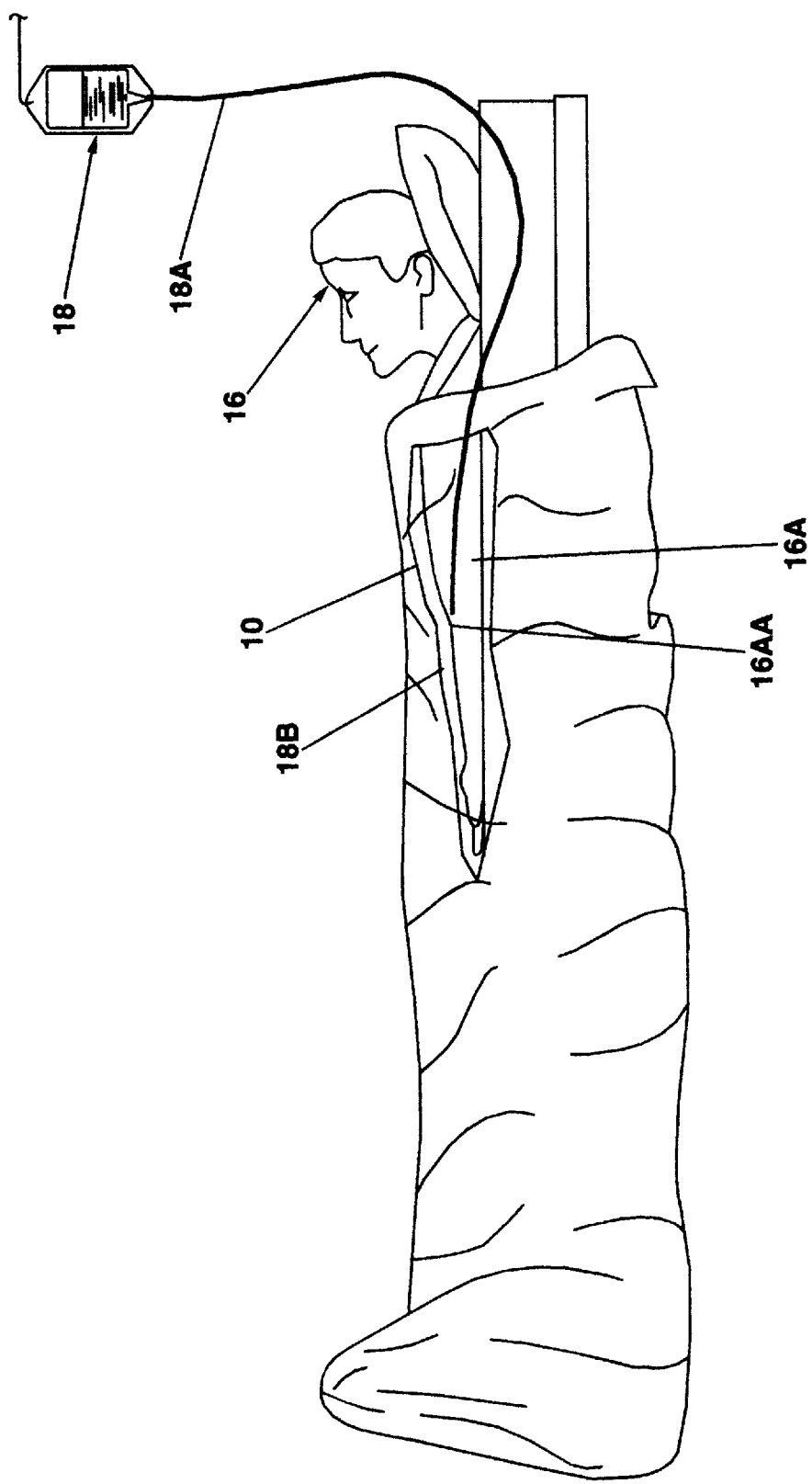
FIG. 1 is a side view of a patient laying in a hospital bed with a blanket with permeable window there over exhibiting an intravenous needle of an intravenous tube inserted into a patient appendage vein of a patient appendage.
Figure 2:
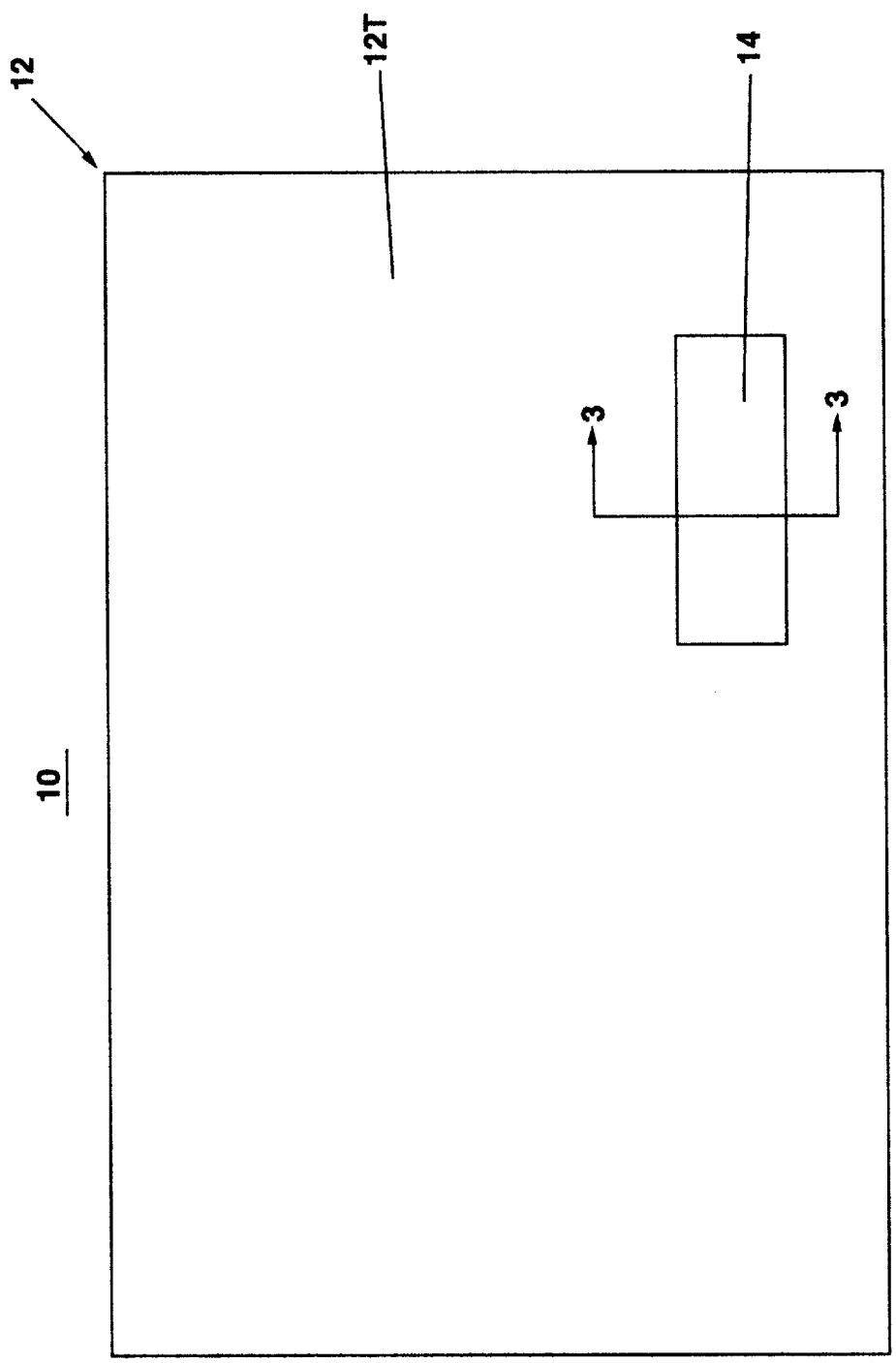
FIG. 2 is a top view of a blanket with permeable window.

Firstly, referring to FIG. 1 which is a side view of a patient (16) laying in a hospital bed with a blanket with permeable window (10) there over exhibiting an intravenous needle (18B) of an intravenous tube (18A) inserted into a patient appendage vein (16AA) of a patient appendage (16A). Referring to FIG. 2 which is a top view of a blanket with permeable window (10). The blanket with permeable window (10) comprises a blanket (12).

The blanket with permeable window (10) further comprises a permeable transparent window (14) positioned within the blanket (12). A periphery of the permeable transparent window (14) is securely attached to the blanket (12) by at least one fastener (20). The permeable transparent window (14) may optionally be multiple in number. The permeable transparent window (14) functions to allow viewing of an intravenous tube (18A) and intravenous needle (18B) of an intravenous (18) which is positioned within a patient appendage vein (16AA) of a patient appendage (16A) of a patient (16). The permeable transparent window (14) is selected from a group consisting of screen, perforated material, and perforated material which is hydrophobic on an exterior and hydrophilic on an interior permitting perspiration to escape from a patient. The permeable transparent window (14) is manufactured from a material consisting of plastic, plastic composite, rubber, and rubber composite. The permeable transparent window (14) is preferably nylon or plastic screening.

Figure 3A:
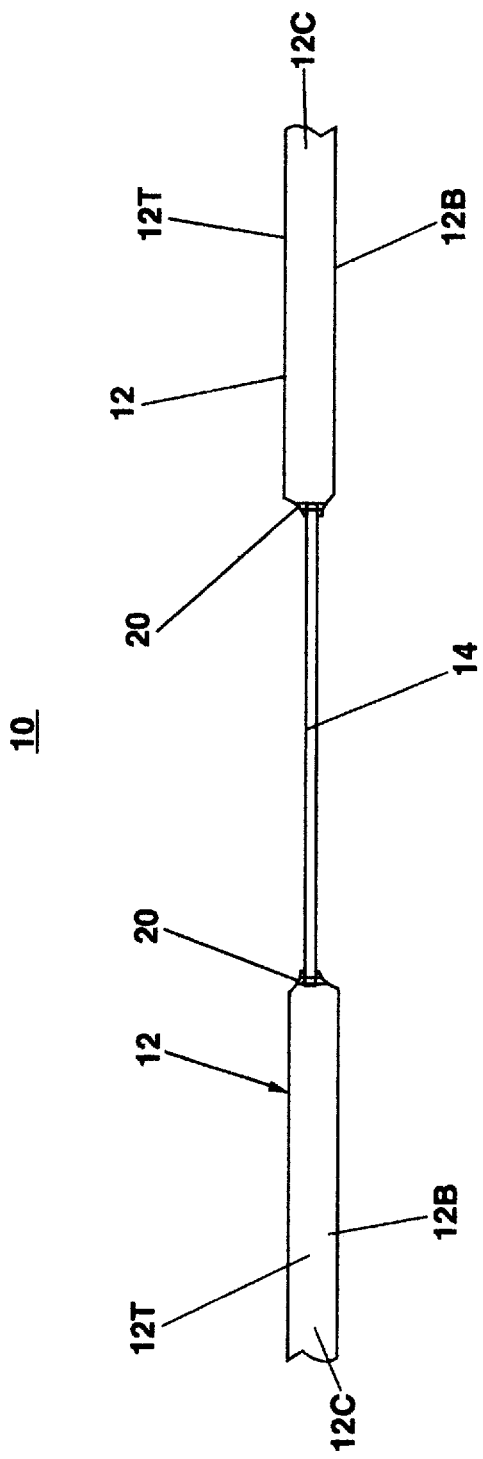
FIG. 3A is a cross-sectional view of a blanket with permeable window along line 3—3 of FIG. 2.
Figure 3B:
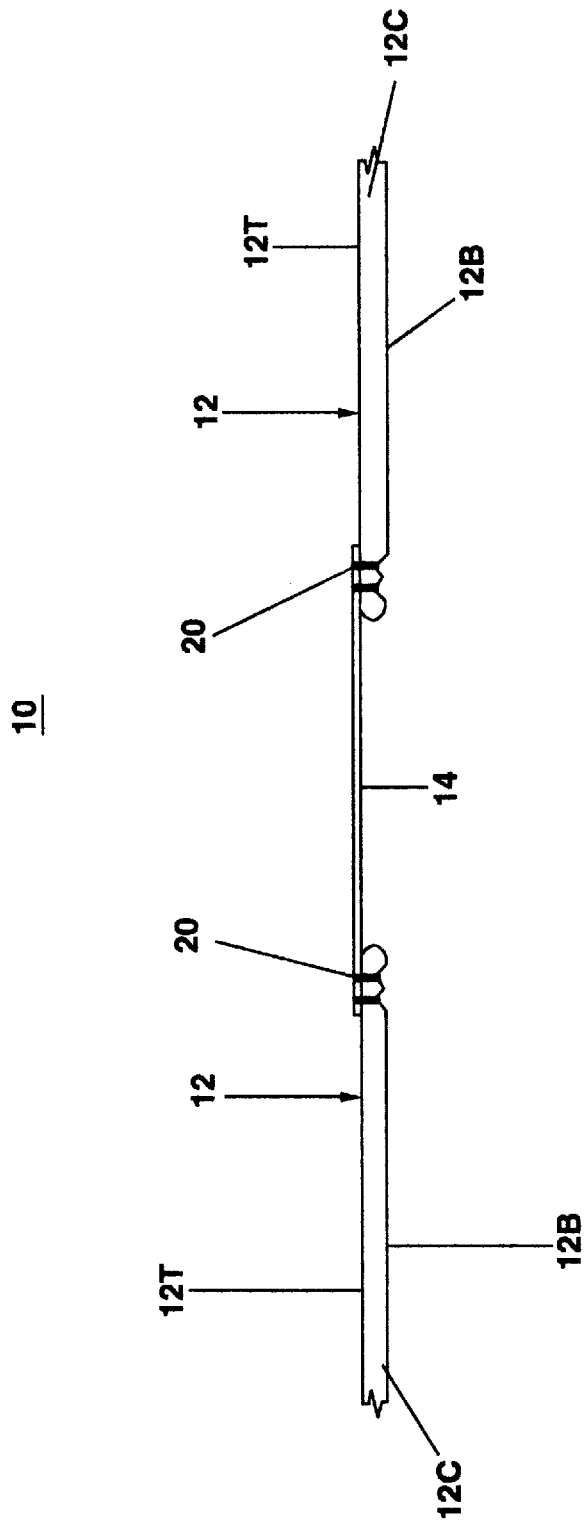
FIG. 3B is a cross-sectional view of a blanket with permeable window attached to a blanket top by at least one fastener.

Lastly, referring to FIG. 3A which is a cross-sectional view of a blanket with permeable window (10) along line 3—3 of FIG. 2. Referring to FIG. 3B which is a cross-sectional view of a blanket with permeable window attached to a blanket top (12T) by at least one fastener (20). The blanket (12) comprises a blanket top (12T) and a blanket bottom (12B) wherein a top of the periphery of the permeable transparent window (14) is securely attached to the blanket top (12T) by at least one fastener (20) to the blanket top (12T) and a bottom of the periphery of the permeable transparent window (14) is securely attached to the blanket bottom (12B) by at least one fastener (20). The blanket (12) further comprises blanket fill (12C) positioned between the blanket top (12T) and the blanket bottom (12B). The blanket fill (12C) is selected from a group consisting of a pneumatic envelope, air filled honey comb, natural fibers and synthetic fibers.

It will be understood that each of the elements described above, or two or more together, may also find a useful application in other types of constructions differing from the type described above.

While the invention has been illustrated and described as embodied in a blankets with windows, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims:

What is claimed is:

1. A blanket with permeable window (10) comprising:

A) a blanket (12) which comprises a blanket top (12T) and a blanket bottom (12B), the blanket (12) further comprises blanket fill (12C) positioned between the blanket top (12T) and the blanket bottom (12B);

B) at least one permeable transparent window (14) is positioned within the blanket (12), a periphery of the at least one permeable transparent window (14) is securely attached to the blanket (12) by at least one fastener (20), a top of the periphery of the permeable transparent window (14) is securely attached to the blanket top (12T) by at least one fastener (20) to the blanket top (12T), a bottom of the periphery of the permeable transparent window (14) is securely attached to the blanket bottom (12B) by at least one fastener (20), the at least one permeable transparent window (14) functions to allow viewing of an intravenous tube (18A) and intravenous needle (18B) of an intravenous (18) which is positioned within a patient appendage vein (16AA) of a patient appendage (16A) of a patient (16).

2. The blanket with permeable window (10) as described in claim 1, wherein the blanket fill (12C) is selected from a group consisting of a pneumatic envelope, air filled honey comb, natural fibers and synthetic fibers.

3. The blanket with permeable window (10) as described in claim 1, wherein the at least one permeable transparent window (14) is selected from a group consisting of screen, perforated material, and perforated material which is hydrophobic on an exterior and hydrophilic on an interior permitting perspiration to escape from a patient.

4. The blanket with permeable window (10) as described in claim 3, wherein the at least one permeable transparent window (14) is manufactured from a material consisting of plastic, plastic composite, rubber, and rubber composite.

* * * * *